United States Patent [19]

Ribi et al.

[11] Patent Number: 4,505,899
[45] Date of Patent: Mar. 19, 1985

[54] REFINED DETOXIFIED ENDOTOXIN PRODUCT

[75] Inventors: Edgar E. Ribi; John L. Cantrell, both of Hamilton, Mont.

[73] Assignee: Ribi ImmunoChem Research, Inc., Hamilton, Mont.

[21] Appl. No.: 586,663

[22] Filed: Mar. 6, 1984

Related U.S. Application Data

[63] Continuation of Ser. No. 382,406, May 26, 1982, Pat. No. 4,435,386.

[51] Int. Cl.³ .................. A61K 37/00; C07G 7/00
[52] U.S. Cl. ............................... 514/8; 260/112 R
[58] Field of Search ............... 424/177; 260/112 R

[56] References Cited

U.S. PATENT DOCUMENTS 4,435,386  3/1984  Ribi et al. ...................... 424/177

Primary Examiner—Delbert R. Phillips
Attorney, Agent, or Firm—Burgess, Ryan & Wayne

[57] ABSTRACT

A pharmaceutical composition comprising refined detoxified endotoxin, trehalose dimycolate, and an acetone precipitated by-product of endotoxic glycolipids extracted with chloroform-methanol (ACP) is disclosed which is useful for the treatment of cancerous tumors. Methods of using the composition for these purposes are also disclosed.

12 Claims, No Drawings

REFINED DETOXIFIED ENDOTOXIN PRODUCT

This is a continuation of application Ser. No. 382,406, filed May 26, 1982, now U.S. Pat. No. 4,435,386.

BACKGROUND OF THE INVENTION

The present invention is directed to a pharmaceutical composition containing three components. The first component is refined detoxified endotoxin (RDE) characterized as having no detectable 2-keto-3-deoxyoctanoate and having between about 350 and 475 nmoles/mg of phosphorus and between about 1700 and 2000 nmoles/mg of fatty acids. The second component is trehalose dimycolate (TDM). The third component of the composition is an acetone precipitated by-product of endotoxic glycolipids extracted with chloroform-methanol (ACP). The foregoing composition is a highly potent anti-tumor composition which is useful in the treatment of cancerous tumors in animals and in humans.

Endotoxic extracts obtained from Enterobacteriaciae including parent organisms and mutants are known. These extracts have been used for immunotherapy of various immunogenic tumors [see *Peptides as Requirement for Immunotherapy of the Guinea-Pig Line-10 Tumor with Endotoxins;* Ribi, et al, Cancer Immunol. Immunother. Vol. 7, pgs. 43-58 (1979) incorporated herein by reference]. However, the endotoxin extracts are known to be highly toxic and, therefore, of limited use in the treatment of cancerous tumors. Efforts have been made to "detoxify" the endotoxins while retaining their tumor regressive capacity. As shown, in Ribi, et al, chemical procedures known to detoxify endotoxins while retaining adjuvanticity, such as succinylation and phthalylation resulted in both loss of endotoxicity and tumor regressive potency. Therefore, prior art attempts to obtain an endotoxin product with high tumor regressive potency and little or no toxicity have thus far not been successful.

Acetone precipitated by-product of endotoxic glycolipids extracted with chloroform-methanol (ACP) does not possess tumor-regressive properties when used alone or in combination with trehalose dimycolate. For a more complete discussion of ACP, its properties and methods of production, reference is made to the above-mentioned Ribi, et al publication.

It is, therefore, an object of the present invention to produce a pharmaceutical composition containing a refined detoxified endotoxin product in combination with ACP and TDM which has a high tumor regressive potency without toxic side effects normally associated with endotoxin products.

It is another object of the invention to provide methods of treating animals and humans with the aforementioned composition to obtain regression or remission of tumor growths.

SUMMARY OF THE INVENTION

The present invention is directed to a pharmaceutical composition comprising RDE having no detectable 2-keto-3-deoxyoctanoate, between about 350 and 475 nmoles/mg of phosphorus and between about 1700 and 2000 nmoles/mg of fatty acids in combination with TDM and ACP. The composition is effective in the treatment of cancerous tumors in warm blooded animals.

Endotoxin extracts of the type used as a starting material to produce refined detoxified endotoxin as previously described may be obtained from any Enterobacteriaciae including parent organisms and mutants. By way of example, the following genera are illustrative of the type of microorganisms that may be used:

Salmonella, Shigella, Escherichia, Brucella, Bordetella, Citrobacter, Psuedomonas, Pasturella, Neisseria, Proteus, Klebsiella, and Serratia.

The following species are typically employed:

*S.minnesota, S.typhimurium, B.pertussis, B.abortus, S.enteritidis, E.coli, S.typhi, S.marcescens, S.typhosa, Shigella flexni,* and *S.abortus equi.*

The endotoxic extracts used as a starting material may be prepared by one of several known methods [see, for example, Webster, M. E., Sagin, J. F., Landy, M., and Johnson, A. G., *J. Immunol.* 1955, 744, 55; Westphal, O., Luderitz, O., and Bister, F., *Z. Naturforsch,* 76 148 (1952); Westphal, O., Pyrogens, in *Polysaccharides in Biology, Tr. Second Macy Conference* (George F. Springer, ed.), Madison, N.J. Madison Printing Co., 1957, 115; Galanos, C., Luderitz, O., Westphal, O., *Eur. J Biochem.* 9, 245 (1969); Chen, C. H., Johnson, A. G., Kasai, N., Key, B. A., Levin, J., Nowotny, A., *J. Infect. Dis* 128 543 (1973); Ribi, E., Haskins, W. T., Landy, M., Milner, K. C., *The Journal of Experimental Medicine* 114 647 (1961); Leive, L., *Biochem. Biophys. Res. Comm.* 21 290 (1965); and Ribi, E., Milner, K. C., and Perrine, T., *J. Immunol.* 82 75 (1959)].

The preferred method of obtaining the endotoxic extract is that disclosed by Chen, et al; namely, methanol-chloroform precipitation.

The methanol-chloroform precipitate (MCP) is reacted with an organic or inorganic acid and then lyophilized to produce a hydrolyzed crude lipid A with reduced toxicity and pyrogenicity as compared with the starting endotoxin material. This product is then treated with a solvent which dissolves fatty acids and other impurities without dissolving the crude lipid A material. The phosphate content of the detoxified, refined lipid A is about one half that observed for toxic endotoxin suggesting that the phosphate content is related to the toxic effects of endotoxins.

The preferred inorganic acids used to react with MCP are hydrochloric acid, sulfuric acid or phosphoric acid and the preferred organic acids are toluene sulfonic acid or trichloroacetic acid. The reaction may be suitably conducted at a temperature between about 90° and 130° C. for a time sufficient to complete hydrolysis usually between about 15 and 60 minutes.

The preparation of crude detoxified endotoxin may also be accomplished by reacting the starting material with the acid in the presence of an organic solvent such as chloroform, methanol, and ethanol or combinations thereof.

The resulting crude lipid A is dissolved in a solvent which can dissolve fatty acids without dissolving the crude lipid A. Acetone is particularly suited for this purpose. The solvent is then removed to produce crude detoxified endotoxin.

The crude detoxified endotoxin is then dissolved in a solvent and passed through a suitable chromatographic column such as a molecular exclusion chromatographic column, to separate the RDE fractions which are then combined after removal of the solvent. In one embodiment, the crude detoxified endotoxin solution is passed through a Sephadex column in the presence of a solvent such as chloroform, methanol, acetone, pyridine, ether or acetic acid or combinations thereof. The pressure of the column may vary but is typically in the range of between about atmospheric and 100 lbs/in$^2$ and the flow rate is between about 0.1 and 10 ml/min.

In another embodiment, the crude detoxified endotoxin solution is passed through a DEAE-cellulose column under the same pressure conditions as mentioned above for the Sephadex column. The flow rate may be maintained between about 2 and 15 ml/min. The solvents used are also the same as those used for the Sephadex column although water or diethylamine can be added to all mixtures at a concentration of up to about 1%.

Other methods of producing RDE from crude detoxified endotoxin include passing the solution through a low pressure silica-gel 60 column having a particle size of between about 15 and 63 microns and using a solvent comprised of chloroform, methanol, water and ammonium hydroxide in a preferred volume ratio of about 50:25:4:2.

The second component of the instant composition, trehalose dimycolate (TDM), may be obtained from the following organisms as, for example, *M.avium*, *M.phlei*, *M.tuberculosis* (Strain H 37 RV and Ayoma B), *M.bovis* BCG, *M.smegmatis*, *M.kansasii*, *Nocardia rubra*, and *Corynebacterium diphtheria*.

Bacteria such as *M.avium* is grown, harvested and then heat killed. The cell mass in then extracted with several solvents and then an active, solvent soluble, fraction is extracted. This extract is further purified by a series of solvent extractions to provide crude TDM (see, *Biologically Active Components from Mycobacterial Cell Walls. I. Isolation and Composition of Cell Wall Skeleton and Component P$_3$*; Azuma, et al Journal of the National Cancer Institute, Volume 52, pgs. 95–101, (1974) incorporated herein by reference). As disclosed in Azuma, et al, crude TDM may then be further purified by centrifugal microparticulate silica gel chromatography to give purified TDM.

The third component of the composition is an acetone precipitated by-product of endotoxic glycolipids extracted with chloroform-methanol (ACP). As previously stated, the Ribi, et al publication more particularly discloses its composition and methods of preparation and is incorporated herein by reference. ACP can be prepared from any Enterobacteraciae previously referred to under the description for RDE.

RDE, TDM and ACP are combined to form a composition having potent anti-tumor activity. The cancers which may be treated by the RDE-ACP-TDM composition include animal tumors, such as bovine squamous cell carcinoma, bovine fibrosarcoma, equine sarcoid, equine melanoma, equine squamous cell carcinoma, canine mammary tumors, canine adenoma and canine melanoma.

The composition is administered by injection in a pharmaceutically acceptable medium such as an oil droplet emulsion* and is preferably administered directly into the tumor under conditions more particularly described as follows.

*The composition may be stabilized as, for example, by a lyophilization procedure and then reconstituted without loss of potency.

The amount of RDE in a single injection for the treatment of animals is between about 6.25 and 250 micrograms/ml. The amount of ACP is between about 375 and 750 micrograms/ml. and the amount of TDM is between about 125 and 250 micrograms/ml. The number of milliliters of the biologic injected into the tumor is determined by the size of the tumor in accordance with the following table:

| Animal Dosage According to Tumor Size | |
|---|---|
| Diameter of Tumor (cm) | Amount of Biologic Injected |
| 0–1 cm | up to 0.5 ml |
| 1–2 cm | 0.5 to 2.5 ml |
| 2–3 cm | 2.5 to 5 ml |
| 3–5 cm | 5 to 10 ml |
| 5–8 cm | 10 to 15 ml |
| greater than 8 cm | 15 to 20 ml |

The maximum dose per injection is about 4500 micrograms for RDE, about 4500 micrograms for ACP and about 1500 micrograms for TDM. The course of treatment comprises up to 5 injections administered at one week intervals.

RDE-ACP-TDM in a suitable injectable medium such as an oil droplet emulsion may be administered directly into tumors. The amount of RDE and ACP, respectively, in a single injection is between about 50 and 1000 micrograms. The amount of TDM which may be administered in a single injection is between about 50 and 300 micrograms. The preferred single dosage level for RDE and TDM is between about 125 and 175 micrograms while the preferred single dosage level for ACP is between about 275 and 325 micrograms each based on a typical 70 kg. adult patient. The injections are administered about once every a week for up to a total of 15 injections. Generally, it is advisable to administer the composition containing between about 50 and 500 micrograms/ml of RDE, between about 50 and 500 micrograms/ml of ACP, and between about 50 and 150 micrograms/ml of TDM per injection.

As described above the composition for treatment of warm blooded animals and humans may be used in the form of an oil droplet emulsion. The amount of oil used is in the range of between about 0.5 and 3.0 percent by volume based on the total volume of the composition. It is preferred to use between about 0.75 and 1.5 percent by volume of the oil. Examples of such oils include light mineral oil, squalane, 7-n-hexyloctadecane, Conoco superoil and Drakeol 6 VR mineral oil (produced by the Pennreco Company, Butler, Pa.).

The homogenized oil containing mixture is then combined with a detergent which may optionally be dissolved in a saline solution prior to mixing. The amount of detergent is typically between about 0.02 and 0.20 percent by volume and preferably between about 0.10 and 0.20 percent by volume based on the total volume of the composition. Any common detergent material may be used including Tween-80, and Arlacel (produced by the Atlas Chemical Company).

The mixture resulting from the addition of detergent is then homogenized to form a suspension which has a high percentage of oil droplets coated with RDE and CWS as determined by observation under a microscope.

The following examples are for illustrative purposes only and are not intended to limit or in any way redefine the invention as claimed in the claims appended hereto.

EXAMPLE 1

Preparation of Crude Detoxified Endotoxin

A 650 mg sample of a methanol-chloroform precipitate produced in accordance with the procedure of Chen, et al *J. Infect. Dis.* 128 543 (1973) was suspended in 150 ml of 0.1N HCl, in a three necked round bottom flask fitted with a condenser, and immersed in a sonicator. After sonication, the glass apparatus was then lowered into an oil bath maintained at 120° C. which allowed the interior temperature of the flask to approach or exceed the boiling point of the solution. Superheating of the solution was minimized by fitting the flask with a capillary tube attached to a nitrogen gas source through one of the necks. A continuous flow of nitrogen was maintained throughout the hydrolysis procedure.

Hydrolysis was continued for 30 minutes, after which the solution was cooled in an ice bath, sonicated to disperse the solid material and distributed in corex tubes. The flask was washed with distilled water to remove all solid material adhering to the sides of the flask, and the wash was added to the suspension in the corex tubes. Centrifugation was carried out at 12,000 rpm for 80 minutes. The supernatant was decanted and discarded. The solid residue was resuspended in distilled water, sonicated until the suspension was well dispersed and recentrifuged. The centrifugation process was then repeated. The residue was taken up in distilled water, shell frozen and lyophilized yielding 382 mg of crude lipid A. 150 mg of this material was treated with cold (0° C.) acetone to remove fatty acids, sonicated, and filtered through a Whatman No. 1 gravity filtration apparatus at 5° C. 100 mg of crude detoxified endotoxin remained after drying.

EXAMPLE 2

Preparation of Crude Detoxified Endotoxin

A 120 mg sample of MCP (methanol-chloroform precipitate) was suspended in 12 ml of absolute methanol, sonicated to disperse solid materials and distributed into 6 (1×10 cm) screw cap vials. 2 ml of 0.2N HCl were added to each tube and the resulting suspension was incubated in a boiling water bath for 45 minutes. After hydrolysis, the tubes were cooled in an ice water bath and centrifuged for about 10 minutes at 2500 rpm. The supernatant was decanted and 5 ml of a 2:1 chloroform/methanol mixture were added to the residue to effect dissolution. 2 ml of water were added per tube and the solution was mixed. The biphasic solution was recentrifuged at 2500 rpm for 10 minutes. The upper water phase was discarded and 1 ml of a 4:1 chloroform/methanol mixture was added to each tube resulting is a clear solution. The solutions were pooled, and the solvent evaporated on a rotary evaporator. The residue was dried under high vacuum and lyophilized to yield 45 mg of crude lipid A. 20 mg of this material were treated with cold (0° C.) acetone, sonicated, and filtered through a Whatman No. 1 gravity filtration apparatus at 5° C. 13 mg of crude detoxified endotoxin remained after drying.

EXAMPLE 3

Preparation of Refined Detoxified Endotoxin 110 g LH-20-100 (25–100 micron particle size: Pharmacia) were combined with 600 ml of a 2:1 chloroform/methanol mixture which was permitted to stand for 30 minutes. The resulting slurry was added to a 25×1000 mm glass chromatography column (BRL Laboratories) fitted with pressure fittings. After packing was completed, the column was attached by means of Teflon pressure tubing to an ISCO Model 132 pump. 400 ml of a 4:1 chloroform/methanol mixture were pumped through the column at the rate of 3 ml/min. 100 mg of crude detoxified endotoxin prepared in accordance with Example 1 were applied to the column in 2.5 ml of a 4:1 chloroform/methanol mixture via a sample loop. The flow was reduced to 1 ml/min. and after 150 ml of eluant were collected, the effluent was connected to a fraction collector. 4 ml fractions were collected and refined detoxified endotoxin fractions were determined by thin layer chromatographic analysis of the fractions [E. Merck, 0.25 mm thick, chloroform/methanol/$H_2O$/$NH_4OH$ (50:25:4:2) as eluant].

The refined detoxified endotoxin fractions were combined and the solvent evaporated leaving 30 mg of refined detoxified endotoxin as a white powder.

EXAMPLE 4

Preparation of Refined Detoxified Endotoxin 33 g of DEAE-cellulose (Whatman DE-32) were suspended in 150 ml of glacial acetic acid and agitated gently for 10 minutes to obtain a slurry powder. The mixture was set aside overnight.

The slurry was poured into a 25×400 mm column, allowed to settle with tapping, and excess acid was thereafter drained. The column was washed with 2000 ml of methanol followed by 200 ml of a 4:1 chloroform/methanol mixture. A 100 mg sample of crude detoxified endotoxin produced in accordance with Example 1 was added to the column in 3 ml of a 4:1 chloroform/methanol mixture or an 80:20:1 mixture of chloroform, methanol and water. The column was eluted with 350 ml of a 4:1 chloroform/methanol mixture followed by 300 ml of a 99:1 methanol/water mixture. Using a linear gradient apparatus, the column was eluted with 2000 ml of a linear gradient starting with 100% methanol and ending with 0.2M acetic acid in methanol. The column was eluted at the rate of 6 ml/min. and 15 ml fractions were collected. Every other fraction was analyzed for total phosphorus content according to the procedure of Bartlett, G. R., *J. Biol. Chem.* 234, 466–471 (1959). The fractions were pooled and evaporated on a rotary evaporator to near dryness and taken up in 10 ml of a 2:1 chloroform/methanol mixture and 40 ml of 0.001M acetic acid in a separatory funnel. The lower layer was separated, filtered through Whatman No. 2 filter paper and evaporated to dryness to yield 19.2 mg of refined detoxified endotoxin.

EXAMPLE 5

8 Strain-2 guinea pigs having Line-10 tumor growths of about 9 mm were injected once with 0.4 ml containing 150 micrograms of each of RDE and ACP and 50 micrograms of TDM directly into the tumor tissue.

At the conclusion of the administration period, each of the guinea pigs were examined to determine the effect of the injection therapy on the tumor growth. Fourteen of the fifteen experimental animals exhibited total regression of the tumor growth.

Control experiments were set up on two groups of 6 Strain-2 guinea pigs having Line-10 tumor growths of the same size as described above. The first group of six guinea pigs was injected once with 0.4 ml containing 50 micrograms each of RDE and TDM. The second group of six guinea pigs was injected once with 0.4 ml containing 50 micrograms of RDE alone. At the conclusion of the test, each of the guinea pigs was examined to determine the effect of the control on tumor growths. All twelve guinea pigs showed no evidence of regression or remission of tumor growths.

What we claim is:

1. A therapeutic composition for imparting immunotherapy comprising an effective amount of each of:
   (a) refined detoxified endotoxin having no detectable 2-keto-3-detoxyoctanoate, between 350 and 475 nmoles/mg of phosphorus and between 1700 and 2000 nmoles/mg of fatty acids;
   (b) an acetone precipitated by-product of endotoxic glycolipids extracted with a mixture of chloroform and methanol;
   (c) trehalose dimycolate; and a pharmaceutically acceptable carrier.

2. The composition of claim 1, wherein the effective amount of refined detoxified endotoxin is up to about 4500 micrograms, the effective amount of said acetone precipitated by-product is up to about 4500 micrograms and the effective amount of trehalose dimycolate is up to about 1500 micrograms.

3. The composition of claim 1, wherein the composition is in lyophilized form.

4. The composition of claim 1 in the form of an oil droplet emulsion.

5. The composition of claim 4, wherein the amount of oil is in the range of 0.5 to 3.0% by volume based on the total volume of said composition.

6. A method for imparting immunotherapy in a warm blooded animal having an immunogenic tumor comprising administering the composition of claim 1 into said warm blooded animal by injection into said immunogenic tumor.

7. A method for imparting immunotherapy in a warm blooded animal having an immunogenic tumor comprising administering the composition of claim 2 into said warm blooded animal by injection into said immunogenic tumor.

8. A method for imparting immunotherapy in a warm blooded animal having an immunogenic tumor comprising administering the composition of claim 3 into said warm blooded animal by injection into said immunogenic tumor.

9. A method for imparting immunotherapy in a warm blooded animal having an immunogenic tumor comprising administering the composition of claim 4 into said warm blooded animal by injection into said immunogenic tumor.

10. The method of claim 6, further comprising administering said composition containing between about 6.25 and 250 micrograms/ml of refined detoxified endotoxin, between about 375 and 750 micrograms/ml of said acetone precipitated by-product and between about 125 and 250 micrograms/ml of trehalose dimycolate by injection into said warm blooded animal.

11. The method of claim 10, wherein said composition is injected up to 5 times.

12. The method of claim 11, wherein said injections are made at intervals of one week.

* * * * *